United States Patent [19]

Martinez Roldan et al.

[11] 4,029,807

[45] June 14, 1977

[54] COMPOUNDS 5-HYDROXYTRYPTOPHAN GLUTAMATE AND ITS DERIVATIVES

[75] Inventors: Cristóbal Martinez Roldán; Miguel Fernandez Braña; José Maria Castellano Berlanga, all of Madrid, Spain

[73] Assignee: Laboratorios Made, S.A., Spain

[22] Filed: Apr. 8, 1975

[21] Appl. No.: 566,085

[52] U.S. Cl. .................. 424/274; 260/326.14 T
[51] Int. Cl.$^2$ ........................... A01N 9/22
[58] Field of Search ............ 260/326.14 T; 424/274

[56] References Cited

UNITED STATES PATENTS 3,847,941  11/1974  Brana et al. ............. 260/326.14 T

OTHER PUBLICATIONS

A.E.C. Societe de Chimie Organique et Biologique, "Chem. Abstracts," vol. 58, p. 1319e (1963).
Gall, "Chem. Abstracts," vol. 78 pp. 279–280, No. 47,812s (1973).
Desoye, "Chem. Abstracts," vol. 72, p. 251, No. 15,759g (1970).

*Primary Examiner*—Ethel G. Love
*Attorney, Agent, or Firm*—Marn & Jangarathis

[57] ABSTRACT

The invention relates to the compound 5-Hydroxytryptophan Glutamate, having anti-depressive action.

3 Claims, No Drawings

COMPOUNDS 5-HYDROXYTRYPTOPHAN GLUTAMATE AND ITS DERIVATIVES

The present invention relates to the industrial production of 5-hydroxytryptophan glutamate and its derivatives.

These compounds have the general formula:

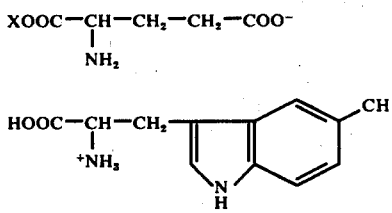

wherein X is hydrogen, alkaline or alkaline-earth metals, or organic compounds of a basic character.

The general method for the synthesis of these compounds is based on the dissolution, jointly or separately, of the acid and the base in the smallest possible quantity of a suitable solvent. This solution can be neutralized by any type of basic organic or inorganic compound, or can be used as it stands. Any of the above-mentioned solutions can be deep-frozen in order to isolate the required product.

The following example illustrates the invention which is not limited thereto.

Example

X = H.

Although the reaction was carried out in various solvents, both organic and inorganic, the example to be cited is that carried out in water, since this solvent is one of the best.

1.47 g (0.01 mol) of glutamic acid (in any of its L, D or racemic forms) together with 2.20 g (0.01 mol) of 5-hydroxytryptophan (in any of its L, D or racemic forms) was dissolved in 100 ml of distilled water at a temperature of 35° C. To promote dissolution vigorous agitation was carried out using an electro-magnetic stirring means or a standard laboratory stirring means connected to a motor. The solution was filtered and the filtered liquid was freeze-dried at ambient temperature and at a pressure of $2 \times 10^{-2}$ mm Hg.

The monohydrated salt, in the form of broad white needles, was obtained with a practically quantitative yield and had a melting point of 148° — 150° C.
Analysis:
Calculated for $C_{16}H_{21}N_3O_7 \cdot H_2O$ C.-49,86; H.-6,01; N.-10.90 Actual: C.-50.38; H.-6.22; N.-10.74.

In the view of the Applicant, the product obtained by this method is new, and in the specific uses for which it is intended it has the advantage of great tolerability, vigorous pharmacological activity and ready solubility in water.

L-5 hydroxytryptophan monohydrate L-glutamate is a new synthetic compound in which glutamic acid potentiates the antidepressive action of L-5 hydroxytryptophan.

1 - Introduction

Serotonin (5-OH-tryptamine) is a neurotransmitting agent principally distributed in the mesencephalon, diencephalon and rhinencephalon, areas which control and modulate the autonomic nervous system (Hess, 1954; Koada, 1951; Gloor, 1955; Pribram and Kruger, 1954). Serotonin is formed from tryptophan, which is hydroxylated into 5-OH-tryptophan, the latter being decarboxylated into serotonin by tryptophandecarboxylase. It is presently thought that the psychic tonus of a person is controlled by the level of cerebral serotonin. The hypothesis of serotonin says that there is a direct corelationship between serotonin deficiency in the brain and certain depressive syndromes. This hypothesis is based on the work of Pare and Sandler, 1959, Van Praag, 1962, and Coppen et al., 1963, who established that monoamino-oxydase inhibitors (products which increase the concentration of serotonin and catecholamines in the brain) can have an antidepressive effect.

Imipramine, as well as other tricyclic antidepressive agents, exercises its effect through an increase in the efficient concentration of monoamines on the receiver level, due to the fact that it produces an incorporation blockage (uptake I) on the presynaptic membrane level. Monoamino-oxydase inhibitors produce an increase of several amines, serotonin, agree on which of these amines is responsible for the antidepressive action. Bartonieck thinks it is the increase in serotonin, whereas Pletscher believes it is the increase in noradrenaline. The fact that a potentiation of the antidepressive effects of the MAO inhibitors has been observed on administering tyrptophan and 5-hydroxytryptophan, precursors of serotonin, but not with DOPA, precursor of noradrenaline, speaks in favour of the hypothesis that it is the serotonin level which plays the most important role in depression. Electroconvulsive therapy produces an increase of cerebral serotonin in all the laboratory animal species studied except mice (Garattini and Valzelli, 1971). The serotonin levels were not affected in other organs (liver, lung, intestine). In patients submitted to electroconvulsivant treatments it was demonstrated that the serotonin concentration in the cerebrospinal fluid was higher after the said therapy than before. Summarising the foregoing, it can be observed how all antidepressive treatments have the same operating pattern, i.e., they increase the level of cerebral serotonin. Undenfriend et al. (1957) determined that when 5-hydroxytryptophan is administered to animals, it rapidly penetrates most tissues and, if there is decarboxylase, it is converted into serotonin. Bodanski et al. (1958) succeeded in raising 10 times the level of serotonin in the brains of dogs to which this precursor had been administered. Bazelon used 5-hydroxytryptophan as a precursor of cerebral serotonin, thus saving the step of tryptophan, which, as is known, is a limiting factor on the biosynthesis of serotonin. Ashcroff and Sharman (1960) suggest a possible relationship between the metabolism of tryptophan and depression: the level of "5-hydroxyindoles" fluorimetrically estimated in the cerebrospinal fluid was significantly lower in nine patients with depressive psychosis than in ten non-depressive patients. Depressed patients eliminate less quantity of tryptamine through urine during the depressive phase than after recovery (Copper et al., 1956). Treatment with monoamino-oxydase inhibitors produces an increase in the levels of serotonin in the brains of rats; the increase becomes higher if tryptophan is administered at the same time (Hess and Doepfner, 1961), this fact being clinically demonstrated in patients by Coppen et al. (1963). Persson and Roos described a case of a depressive patient in whom the administration of amitryptiline together with anticonvulsivant therapy, for two months, did not produce any positive response; however, the instauration of treatment with 5-hydroxytryptophan for 5 days (total dose 150 mg) provided a rapid improvement in the state of mind and disappearance of the depressive symptoms was observed two weeks after the said treatment. It is interesting to point out that this patient was previously treated with L-DOPA, precursor of noradrenaline, without obtaining any result. Isamu Sano (1970) treated 107 patients in depressive phase with L-5-hydroxytryptophan for 5 weeks in the form of tablets (10, 50 and 100 mg three times a day), the symptoms remitting so rapidly that even the patients themselves were impressed. The same author treated patients affected by Parkinson's disease with L-5-hydroxytryptophan, finding an intense antidepressive action with improvement of the affective field, of the psychomotor impulse and activation of personal initiative; he also describes a visible anti-tremor effect. Kline and Sacks (1963, 1964) administered DL-5-OH-tryptophan to depressed patients intravenously (10-50 mg), together with a monoamino-oxydase inhibitor, finding spectacular results (improvement of depression in one day obtained with a MAO inhibitor and 5-OH tryptophan, intravenously).

With all this, we explain the operating pattern of our product; this substance raises the levels of cerebral serotonin, in a greater way than the sole administration of L-5-hydroxytryptophan, as is demonstrated by the symptomatology of the animals injected. This product has been compared with another two of the same use: tranilcypromine and imipramine.

2 — Toxicity

The studies of acute toxicity have been made with I.C.R. Swiss albino mice of both sexes. We express the toxicity date with the parameters of lethal dose 16 ($LS_{16}$), lethal dose 50 ($LD_{50}$) and lethal dose 84 ($LD_{84}$), in mg/kg. of weight. The substance was administered intraperitoneally.

|  | $LD_{16}$ | $LD_{50}$ | $LD_{84}$ |
| --- | --- | --- | --- |
| Our product | 260.5 | 323 | 401.4 |
| Tranilcypromine | 7.3 | 11.3 | 18 |
| Imipramine | 33.3 | 51.6 | 80 |

As can be seen from the foregoing table, our antidepressive product is 300 times less toxic than tranilcypromine and 6 times less toxic than imipramine.

3 — Activity a. Irwin's schema

The administration of our product to female mice weighing 28 ± 2 g., at the rate of 10 mg/kg. orally, produces an increase in the state of alertness, a reaction to cleanliness and an increase in spontaneous activity, in addition to restlessness and irritability. These symptoms appear rapidly, 15 minutes after its administration, and last 120 minutes at least.

This symptomatology is not observed with the separate administration of L-glutamic acid and L-5 hydroxytryptophan at doses equimolecular to those tested with our product and the pharmacological activity of the combination is therefore superior to that of each ingredient separately. Neither is this symptomatology observed with tranilcypromine and imipramine.

b. Analgesic activity

Our product has proved to have a significant analgesic action with the techniques of chemical analgesia and thermal analgesia (hot plate at 55° C). At the oral dose of 10 mg/kg. it has the same analgesic effect as dextropropoxyphene at the intraperitoneal dose of 50 mg/kg.

c. Antiserotoninic activity

With the technique of a rat's isolated uterus and at the dose of 40 mcg/ml., we have found a 36% inhibition of the responses to serotonin.

Its peripheral antiserotoninic and central analgesic activity makes our product be particularly useful in migraines.

4 — Indications

Depressive psychosis and schizophrenia.
Neurosis.
Cephaleas of mental illnesses.
Migraines.
Morphine addiction cures.
L-Dopa psychosis.
Alterations of sleep.

5 - Tests comparing activities

Our product is principally indicated in all types of depressions. Its operating pattern is an increase in the levels of intracerebral serotonin. There are many substances which have been used in the field of depressions, but none of them has the same operating pattern.

We give a precursor, which pierces the hematoencephalic barrier and is transformed into serotonin, in the brain.

The most conventional antidepressive agents used so far have been: 1. MAO inhibitors. The most powerful one is TRANILCYPROMINE.

Tranilcypromine

It is a powerful inhibitor of non-hydrazinic MAO. Its operating pattern is different from that of our product. Tranilcypromine has a direct stimulating action on the central nervous system which is responsible for its antidepressive action; to the contrary, since it is a MAO inhibitor, the cerebral serotonin raising action is very inferior to our product. Although it is a powerful antidepressive agent, its clinical use requires much care because of the great amount of adverse effects and secondary reactions which have been described with its use. No interesting secondary reactions have yet been described with L-5-hydroxytryptophan L-glutamate, for which reason the therapeutical margin is greater and more favourable for our product. Imipramine: It is a tricyclic antidepressive agent which exercises its effect through an increase of the efficient concentration of noradrenaline on the receiver level, due to the fact that it produces an incorporation blockage (uptake I) on the presynaptic membrane level. Not all authors agree on which amine is responsible for the antidepressive action (serotonin or noradrenaline). Bartonieck thinks it is the increase in noradrenaline. The fact that a potentiation of the antidepressive effects of the MAO inhibitors has been observed on administering tryptophan and 5-OH tryptophan, precursors of serotonin, but not with DOPA, precursor of noradrenaline, speaks in favour of the hypothesis that it is the serotonin level which plays the most important role in depression.

For all these reasons, we deduce that L-5-hydroxytryptophan L-glutamate is therapeutically superior to tranilcypromine and imipramine.

ASHCROFF, G. W. and SHARMAN, D. F. 5-Hydroxyindoles in human cerebrospinal fluids. Nature, 186, 1.050 – 1.051 (1.960).

AXELROD, J. Metabolism and inactivatin of noradrenaline and adrenaline and the effect of drugs. In Pharmacology of Cholinergic and Adrenergic Transmision. The Macmillan Co., N.Y. 205 (1.965).

BARTONIECK, V. Medna Pharmac. Exp. 14, 365 (1.966).

BAZELON, M. and al. The Lancet, 1130–1133, Mayo 27 (1972).

BODANSKI, D. F. WEISS BACH, H. and UDENFRIEND, S. Pharmacological studies with the serotonin precursor, 5-OH tryptophan, Journal of pharmac. Exp. Ther, 122, 182 – 94 (1.958).

COPPEN, A. SHAW, D. M. and FARRELL, J. P. Potentiation of the antidepressive effect of a monoamine-oxidase inhibition by tryptophan. Lancet 1, 79–80 (1.963).

COPPEN, A. SHAW, D. M. and MALLESON, A. G. Changes in 5-OH-tryptophan metabolism in depression, British Journal of Psychiatry 111, 105–107 (1.965).

GARATTINI, S. VALZELLI, I. Psychotropic Drugs, Edited by Garattini and GHETTI 428, Amsterdam (1.957).

HESS, S. M. and DOEPFNER, W. Behavioural effects and brain amine contents in rats. Arch. int. Pharmacod. 134, 89–99 (1.961).

ISUMU SANO. L-5-hydroxytryptophan (L-5-HTP). Therapie bei endogener Depression. Munch. med. Wschr. 144, 1713–16 (1.972).

ISAMU, S. and KAZUNI, T. L-5-hydroxytryptophan (L-5-HTP) Therapie des Morbus. Parkinson. Munchr. med. Wschr. 114, 1717–1719 (1.972).

KLINE, N. SACKS, W. Relief. of depression within one-day using an MAOI and intravenous 5-HTP. American Journal of Psychiatry 120, 274, 275 (1.963).

KLINE, N. SACKC, W. and SIMPSON, G. M. Further studies on one-day treatment of depression with 5-HTP. American Journal of Psychiatry 121, 379–81 (1.964).

PARE, C. M. B. and SANDLER, M. A clinical and biochemical of a trial of iproniazid in the treatment of depression. J. of Neurology, Neurosurgery and Psichiatry 22, 247–251 (1.959).

PERSSON, T. and ROSS, B. E. "El 5-hidroxitriptofano en la depresion" The Lancet, 987, (1.967).

PLETSCHER, A. Arzneimittel Forch 14, supp 479 (1.964).

PRAAG, H. M. and LEIJNSE, B. Die Bedenteng der Monoamineo xydase-tenming als antidepressives Princp. Psychopharmacologia 4, 1–14 (1.962).

UDENFRIEND, S. and col. Ann. N.Y. Acd. Sci 66–602 (1.957).

UDENFRIEN, S. and col. J. Brul. Chem. 224, 803 (1.957).

Listed below are examples of pharmaceutical compositions containing as active ingredient L-5-hydroxytryptophane monohydrate L-glutamate, combined with carriers and pharmaceutical excipients.

The injectable dose of this product is 75 mcg. per kg. of weight and day. The dose for an average adult will be 5 mg. daily.

The oral dose is 100 mcg. per kg. of weight and day. An average individual will be administered 7.5 mg. daily in three doses of 2.5 mg.

EXAMPLE 1

INJECTABLE: Comprising a freeze-dried vial and an ampoule with solvent.

| Composition of the freeze-dried vial: | | |
|---|---|---|
| L-5-hydroxytryptophane L-glutamate | 5 | mg. |
| Manitol | 45 | mg. |
| Composition of the ampoule with solvent: | | |
| Sodium chloride | 27 | mg. |
| Water for injectables, q.s.q. | 3 | ml. |

EXAMPLE 2

CAPSULES: Hard gelatine.

| L-5-hydroxytryptophane L-glutamate | 2.5 | mg. |
|---|---|---|
| Lactose | 95 | mg. |
| Magnesium stearate | 1 | mg. |

We claim:
1. A compound consisting of 5-hydroxytryptophan glutamate having the general formula

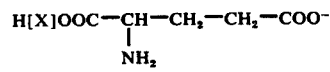

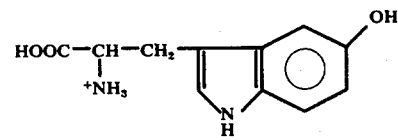

2. A pharmaceutical composition exhibiting antidepressive properties which comprises an anti-depressive amount of a compound as claimed in claim 1 and a pharmaceutically acceptable carrier therefor.

3. A process for alleviating depression in an animal, comprising:
administering to the animal an anti-depressant amount of a compound as defined in claim 1.

* * * * *

UNITED STATES PATENT OFFICE
CERTIFICATE OF CORRECTION

Patent No. 4,029,807     Dated June 14, 1977

Inventor(s) Cristobal M. Roldan et al

It is certified that error appears in the above-identified patent and that said Letters Patent are hereby corrected as shown below:

Col. 1, line 46, delete "10-2" and substitute --$10^{-2}$--.

Col. 2, line 21, after "serotonin," insert --noradrenaline, adrenaline, dopamine, etc.; not all authors--.

Col. 6, line 39, delete "H[X]OOC" and insert --HOOC--. (Claim 1)

Signed and Sealed this

Sixteenth Day of May 1978

[SEAL]

Attest:

RUTH C. MASON
Attesting Officer

LUTRELLE F. PARKER
Acting Commissioner of Patents and Trademarks